United States Patent [19]
Bednarczyk et al.

[11] Patent Number: 5,747,749
[45] Date of Patent: May 5, 1998

[54] ACOUSTIC LOGGING TO IDENTIFY OIL FLOW RATE

[75] Inventors: Adam Bednarczyk, Carrollton; Robert E. Maute, Richardson; Laird B. Thompson, Dallas, all of Tex.

[73] Assignee: Mobil Oil Corporation, Fairfax, Va.

[21] Appl. No.: 764,403

[22] Filed: Dec. 11, 1996

[51] Int. Cl.$^6$ ............................ G01V 1/40; G01F 1/20
[52] U.S. Cl. ............ 181/102; 73/152.32; 73/19.03; 73/19.04; 73/861.19; 73/861.25; 73/861.28; 73/861.31; 175/48; 166/264
[58] Field of Search ................ 73/152.32, 19.03, 73/19.04, 861.19, 861.25, 861.31, 861.28; 175/48; 166/264; 181/102

[56] References Cited

U.S. PATENT DOCUMENTS

| | | | |
|---|---|---|---|
| 3,511,334 | 5/1970 | Zemanek, Jr. | 181/104 |
| 4,433,573 | 2/1984 | Halin | 73/155 |
| 4,480,485 | 11/1984 | Bradshaw et al. | 73/861.28 |
| 4,571,693 | 2/1986 | Birchak et al. | 364/509 |
| 4,736,348 | 4/1988 | Bednarczyk | 367/69 |
| 4,947,683 | 8/1990 | Minear et al. | 73/155 |
| 5,001,676 | 3/1991 | Broding | 367/31 |
| 5,035,147 | 7/1991 | Woodward | 73/861 |
| 5,113,867 | 5/1992 | Janszen | 128/661.09 |

OTHER PUBLICATIONS

Branagan, Paul et al., Tests Show Production Logging Problems in Horizontal Gas Wells, Jan. 10, 1994, Oil & Gas Journal, pp. 41–45.

Hill, A. D. et al., Production Logging Tool Behavior in Two–Phase Inclined Flow, Oct. 1982 Jrnl. of Pet. Tech., pp. 2432–2440.

Kelman, J. S., Biphasic Fluid Studies for Production Logging in Large–Diameter Deviated Wells, Nov. '93, The Log Analyst pp. 6–10.

Ding, Z. X., A Comparison of Predictive Oil/Water Holdup Models For Production Log Interpretation in Vertical and Deviated Wellbores, Jun. 19–22, 1994, SPWLA Logging Symposium, pp. 1–18.

Zhu, Ding et al., The Effect of Flow from Perforations on Two–Flow: Implications for Production Logging, Oct. '88, Society of Petroleum Engineers, pp. 267–275.

*Primary Examiner*—J. Woodrow Eldred
*Attorney, Agent, or Firm*—Malcolm D. Keen

[57] ABSTRACT

A method and apparatus for determining the various components of a multi-phase fluid flow in a defined area includes using an acoustic transceiver tool to direct a beam of acoustic energy toward the fluid flow in a producing well or a horizontal line. A signal is generated when the reflection of the beam of acoustic energy returns and is detected. The signal is rectified and recorded as a measure of oil flow rate within the well. The amplitude peaks are identified and areas around each peak are determined. Two areas of the rectified signal are defined relating to the determined amplitude peaks. The rectified signal under each area is integrated to provide an indication of fluid flow and the strength of the signal reaching the casing. A ratio is determined from the integration results of the two areas. The magnitude of this ratio provides an indication of the extent of the presence of gas in the fluid flow. In an alternate embodiment, the detected signal is rectified and the envelop of the rectified full wavelet of returning signals is taken, reducing the frequency of the signal. The envelop of the reflection signals are recorded as a measure of oil flow rate within the defined area. The amplitude peaks are identified and areas around each peak are defined. Each defined area of the envelop is integrated to determine the portion of the flow that is liquid. A ratio is determined from the integration results of the two areas. The magnitude of this ratio provides an indication of the extent of the presence of gas in the fluid flow.

24 Claims, 3 Drawing Sheets

ACOUSTIC LOGGING TO IDENTIFY OIL FLOW RATE

BACKGROUND OF THE INVENTION

1. Field of the Invention

The present invention pertains to fluid flow measurement in flow lines and more particularly to total fluid, both gas and liquid, flow measurement from various pay zones within a deviated wellbore or a surface line.

2. Related Prior Art

In the producing of an oil well penetrating an oil-bearing subsurface formation, it is often desirable to measure the fluid flow rate from the well. This information indicates the total amount of hydrocarbon fluids that are being produced and the relative quantities of each. These quantities are an indication of the desirability of maintaining a producing well, or whether it should be temporarily taken out of operation until the price of the primary fluid produced, that is the one with the greatest percentage of the total output, increases to make a marginal well profitable. These quantities also can indicate whether a well should be held for a secondary recovery type of production process or merely capped.

Flow meters located on the surface of the earth have been successfully used to carry out such a measurement. However, it is total liquid flow, particularly liquid flow such as oil and water, that is usually measured by such flow meters. Further, in prior art, such measurement must be done on separate samples to obtain both gas and liquid from fluid flow measurement. In addition, prior art has illustrated several ways of measuring fluid flow in wellbores or other flow lines which may combine to provide a total flow. The measurement of fluid flow is often done in wellbores is primarily carried out through the use of logging tools, particularly acoustic logging tools, although the fluid flow nay be measured at the surface. Among acoustic logging tools, one of the most productive is the borehole televiewer. The televiewer rotates an acoustic source several hundred times a minute, producing acoustic pulses to provide an acoustic picture of the walls of the borehole. This picture can indicate a wealth of information regarding the well and surrounding formations.

The following patents are representative of the state of the art relating to fluid flow measurement in hydrocarbon producing wellbores. Although most of these patents deal with down hole measurements, several patents have been included to illustrate the state of the art for surface measurements and laboratory type measurements for completeness.

U.S. Pat. No. 3,454,085, titled "Well Installation with Plural Flow Meters", issued to J. H. Bostock relates to a method and apparatus used in a well installation to provide a measurement of fluid flow between the earth surface and one or more subsurface formations penetrated by a well bore. The well bore is defined by a flow conductor which extends through the well bore, such as a casing. The flow conductor has vertically spaced ports between barriers which close the well bore about the flow conductor between each pair of such earth formations. The ports provide fluid communication between the flow conductor and the subsurface formations. Flow meters mounted on the flow conductor are used to determine the rate of flow of fluid in the flow conductor above or below each port so that the rate of flow of fluids between each such earth formation and the flow conductor can be determined.

U.S. Pat. No. 5,138,585, titled "Method for Fluid Identification and Evaluation Within Wellbores Using Ultrasonic Scanning" issued to Jorg A. Angehru and Charles F. Magnani, relates to a method for using data from a borehole televiewer in an active well to determine flow properties. This method involves determining the wall effects from the data, and factoring out the wall effects from the data to determine the fluid properties.

U.S. Pat. No. 3,603,145, titled "Monitoring Fluids in a Borehole" issued to Billy P. Morris, relates to a method and apparatus for monitoring flow and character of fluids in a borehole that penetrates subterranean formations. This is accomplished by transmitting acoustic energy through the fluids between several transducers in a down-hole tool and discriminating intelligence bits from the acoustic energy arriving at the transducer serving as receiver. A portion of the acoustic energy is transmitted upstream and a portion of the acoustic energy is transmitted downstream. Intermittent acoustic energy is employed and the intelligence bits are, respectively, the travel time downstream and the travel time upstream. This affords information as to the difference in the respective travel times and the average travel time. The difference in travel times is related to the velocity of flow of the fluids. The average travel time is related to the density of the fluids. In another method, either intermittent or continuous acoustic energy is employed and the intelligence bits are respectively, apparent frequency and amplitude. Apparent frequency affords information as to frequency shift which is related to the velocity of fluid flow. Amplitude is related to the fluid density.

U.S. Pat. No. 4,215,567, titled "Method and Apparatus for Testing a Production Stream", issued to Richard J. Vlcek, relates to a method and apparatus for testing a production stream comprised of oil, water, and gas flowing through a conduit to determine their respective percentages. A sample portion of the production stream is pumped through a sample line into a sample chamber where it is heated and allowed to set for a retention period to substantially separate the sample portion into oil and water layers. Gas that evolves from the sample portion is vented from the chamber. At the end of the retention period, the sample portion is pumped back through the sample line into the conduit. As the sample portion flows through the sample line, the oil and water content of the sample and the volume of the sample are measured to determine the oil and water percentages. Also, the volume of the sample portion is measured as it is pumped through the sample line into the sample chamber. By comparing this volume with the volume of the sample portion pumped back into the conduit, the gas-liquid ratio of the sample portion can be determined.

U.S. Pat. No. 3,776,032, titled "Method and Apparatus for Detecting an Inflow of Fluid into a Well", issued to Charles B. Vogel, relates to a method and apparatus for detecting an inflow of fluid into a well during rotary drilling of the well. The inflow of gas is detected by an acoustic detector. The inflow of water is detected by resistivity detection device. The resulting information is transmitted to the surface through pressure pulses produced in the drilling fluid circulated during drilling.

U.S. Pat. No. 3,246,145, titled "Liquid Density Measurement System for Determination of Oil in Water", issued to Robert A. Higgins, relates to a system for determining the relative density of a liquid. The system includes a test chamber into which the liquid is introduced for testing purposes. A radioactive source is positioned on one side of the chamber for directing radiation through the liquid in the chamber. A radiation detector is positioned on the other side of the chamber for detecting radiation passing through the liquid and the chamber. At least a portion of the walls of the chamber between the source and the detector are of material relatively transparent to low energy radiation. With such structure, the low energy radiation is allowed to pass freely from the source through the liquid and to the detector. An energy discriminator responsive to only a predetermined low energy range is interconnected with the detector. A recorder is interconnected with the discriminator for recording an indication of the radiation detected within the low energy range.

None of the foregoing references provide a method of measuring the hydrocarbon fluid flow rate in the total fluid flow in a single non-evasive measurement so as to aid in determining the oil-producing rate and the gas producing rate of the oil-bearing formation. Further, there may be several oil-producing zones within the subsurface formation. None of the foregoing references provide a method for measuring in-situ the oil flow rate contribution and the gas flow rate contribution from each of such zones to the total oil flow rate from the well.

SUMMARY OF THE INVENTION

In practicing the present invention, an acoustic logging tool is used to direct a beam of acoustic energy toward the fluid flow in a producing well or a horizontal line. A signal is generated when the reflection of the beam of acoustic energy returns and is detected. The signal is rectified and recorded as a measure of fluid flow rate within the well. The amplitude peaks are identified and areas around each peak are determined. One area provides an indication of the gas/liquid flow. The other provides an indication of the strength of the acoustic reflection from the casing. The rectified signal is integrated to determine the portion of the flow that is liquid. A ratio is determined from the integration results of the two areas. The magnitude of this ratio provides an indication of the extent of the presence of gas in the fluid flow.

In an alternate embodiment, the signal is rectified and the envelop of the rectified full wavelet of returning signals is taken, reducing the frequency of the signal. The envelop of the reflection signals are recorded as a measure of oil flow rate within the well. The amplitude peaks are identified and areas around each peak are determined. The envelop for each determined area is integrated to provide an indication of fluid flow and an indication of the strength of the casing reflection. A ratio is determined from the integration results of the two areas. The magnitude of this ratio provides an indication of the extent of the presence of gas in the fluid flow.

The present invention provides a method for determining the fluid hydrocarbon flow rate in a producing oil well by using an acoustic logging tool to direct a beam of acoustic energy toward the fluid flow toward the surface from the well. Reflection signals are recorded as a measure of oil flow rate within the well. The full wavelet of returning signals is taken, reducing the frequency of the signal. The signal is divided into two portions and each portion is integrated to determine the casing energy and the gas/liquid energy to determine the portion of the flow that is liquid and the portion of the flow that is gas.

In an alternate embodiment, the envelop of the full wavelet of returning signals is taken, reducing the frequency of the signal. The envelop is divided into two portions and each portion is integrated to determine the casing energy and the gas/liquid energy to determine the portion of the flow that is liquid and the portion of the flow that is gas.

The present invention is directed to an acoustic logging method for determining oil flow in a fluid flow stream such as, an oil producing well penetrating a subsurface formation or a surface production line. A logging tool is placed in a select position within a fluid flow containing hydrocarbons. The logging tool includes a transducer for transmitting and receiving acoustic energy. The transducer transmits compressional wave acoustic energy in a beam into the fluid flow upward through the producing well from the subsurface formation to the surface of the earth. The transducer receives compressional wave reflection signals from oil within the fluid flow and flowing past the transducer toward the surface of the earth. Such reflection signals occur due to the acoustic impedance changes at interfaces within the fluid flow. The reflection signals are rectified and recorded as a measure of the fluid flow rate within the producing well at the selected position of the transducer.

In an alternate embodiment, the reflection signals are rectified and an envelop of the received reflection signals is recorded as a measure of the fluid flow rate within the producing well at the selected position of the transducer.

In a more specific aspect, when the present invention is used in a producing well, the logging tool is moved through the producing well to successively position the transducer above each producing zone and below the perforations for the next higher producing zone within the subsurface formation. At each successive positioning of the transducer, compressional wave acoustic energy is transmitted from the transducer in a beam into the upward fluid flow through the producing well. Reflection signals received by the transducer occurring due to acoustic impedance changes at interfaces within the fluid flow are recorded. These reflection signals are rectified, separated into two sections and the sections are integrated. A ratio is established to determine the gas flow within the fluid flow. The recorded reflection signals along with their ratios are compared for each successive positioning of the transducer to identify the oil flow rate entering the producing well from each oil producing zone.

In the alternate embodiment, the reflection signals are rectified and an envelop of the rectified signals is obtained. The envelop is separated into two sections and the sections are integrated. A ratio is established to determine the gas flow within the fluid flow. The envelop of the recorded reflection signals along with their ratios are compared for each successive positioning of the transducer to identify the oil flow rate entering the producing well from each oil producing zone.

DESCRIPTION OF THE PREFERRED EMBODIMENT

Logging tools appear in many varieties, from neutron logging tools to gamma ray logging tools to resistivity logging tools etc. It can be said that a sub group of all logging tools is acoustical logging tools. Acoustical logging tools can be further divided into at least two categories. The logging tools which use an envelop signal and logging tools that use a full wavelet signal. The present invention deals with the use of both of these types of acoustic logging tools. A borehole televiewer is one type of logging tool that can be used in practicing the present invention. Previously, only the amplitude of the signal from the borehole televiewer has been used to extract the information relating to fluid flow.

In practicing the present invention, the borehole televiewer or similar acoustic device is used to direct a beam of acoustic energy toward the fluid flow in a fluid flow line that may be either a oil producing well or a pipeline. A signal is generated when the reflection of the beam of acoustic energy returns and is detected. The signal is rectified and recorded as a measure of oil flow rate within the line. The amplitude peaks are identified and an area near each peak is defined. The portion of the rectified signal in each area is integrated to determine the area value under the curve defined by the rectified reflection signals. A ratio is determined from the integration results of the two areas. The magnitude of this ratio provides an indication of the extent of the presence of gas in the fluid flow.

In an alternate embodiment, the signal is rectified and the envelop of the rectified full wavelet of returning signals is taken, reducing the frequency of the signal. The envelop of the reflection signals are recorded as a measure of oil flow rate within the well. The amplitude peaks of the envelop are identified and areas around each peak are identified. Each of the two areas of the envelop is integrated to determine the value of each area under the curve defined by the envelop curve. A ratio is determined from the integration results of the two areas. The magnitude of this ratio provides an indication of the extent of the presence of gas in the fluid flow.

Figure 1:
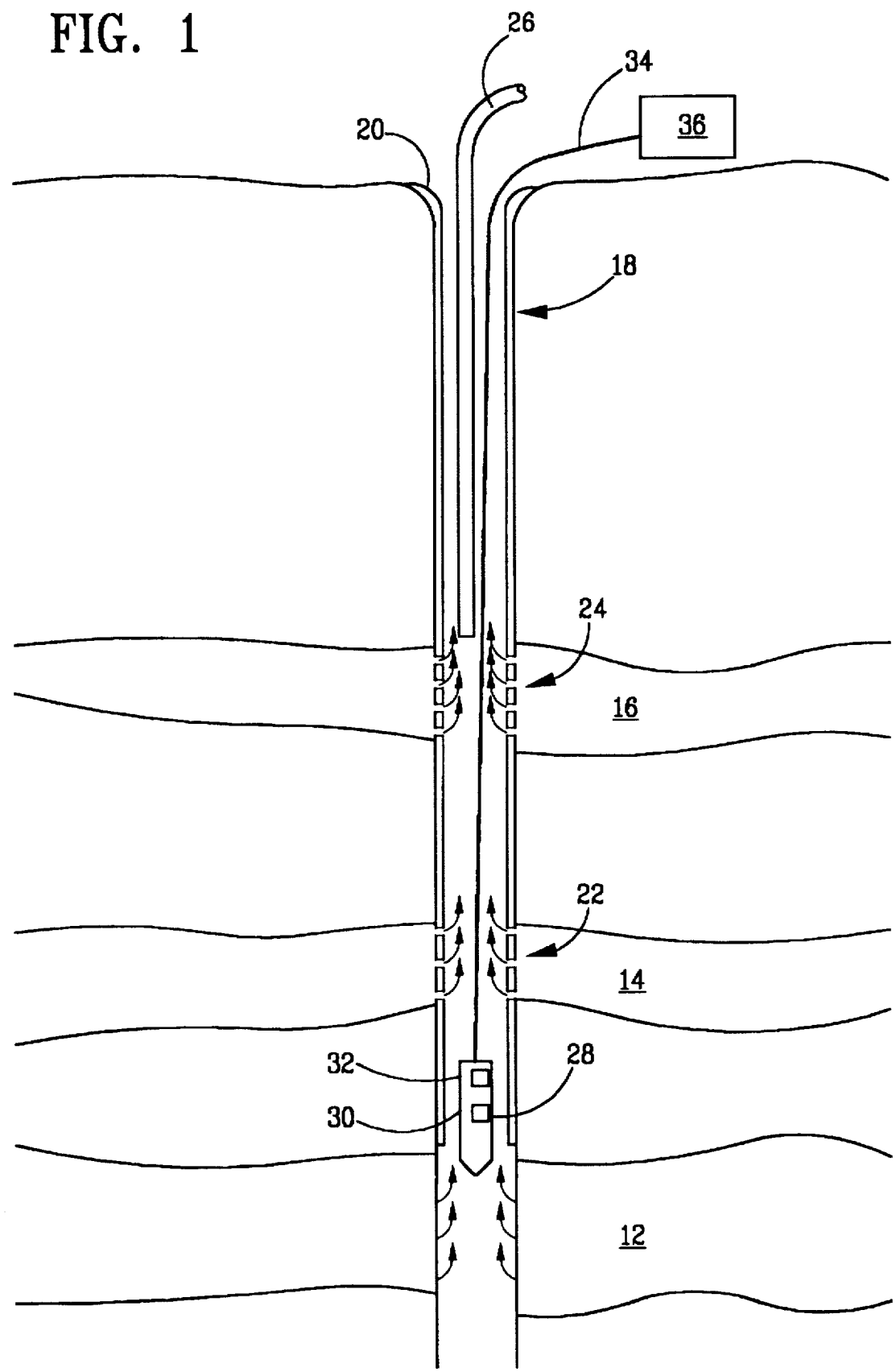
FIG. 1 is a drawing illustrating the positioning of an acoustic logging tool within a borehole penetrating a subsurface oil-bearing formation.

Referring now to FIG. 1, a subsurface formation is shown having a plurality of hydrocarbon producing zones 12, 14 and 16 and is penetrated by a cased borehole 18. Casing 20 of borehole 18 is perforated at locations 22 and 24, adjacent each of the hydrocarbon producing zones 14 and 16, respectively to establish fluid flow from such producing zones into borehole 18 as illustrated by arrows. Such fluid flow, oil, water and gas combined, flows upwardly through the well and exits by way of a conduit 26.

To monitor the oil flow rate in-situ from each of the producing zones in accordance with the present invention, an acoustic logging tool 28, preferably a borehole televiewer, is lowered down borehole 18. Ideally, logging tool 28 is lowered to a position within casing 20 immediately above producing zone 12 and below perforations 22 along the next higher producing zone 14. Logging tool 28 includes a transducer 30 for transmitting and receiving acoustic energy.

Transducer 30 transmits a beam of compressional wave acoustic energy into the upward fluid flow from the producing zone 16. As the beam of acoustic energy enters the fluid flow, it is reflected back toward transducer 30 by acoustic impedance changes at oil-water interfaces within the fluid flow. The transmitted beam of compressional wave acoustic energy is reflected from the surface of an oil or water droplet back toward the transducer 30 as a reflection signal illustrated in FIG. 4. Transducer 30 provides the received reflection signal to electronics 32 where it is rectified. In this application, the envelop of the signal is obtained due to the distance it must be transmitted uphole, although the rectified raw signal is preferred since it contains much more detailed information regarding the fluid flow than the envelop signal.

The envelop signal is transmitted uphole over logging cable 34 to suitable surface electronics 36 where the amplitudes of the envelop of the reflection signals are recorded in correlation with depth.

Logging tool 28 is moved up wellbore 28 to position transducer 30 at a second selected position above the perforations 22 along the producing zone 14 and below the perforations 24 along the next higher producing zone 16. At this position, transducer 30 again transmits a beam of compressional wave acoustic energy into the upward fluid flow through the producing well. At this position the fluid flow is the combined fluid flows from oil-producing zones 16 and 14. Similarly, reflection signals received by transducer 30 from oil and water in the fluid flow. Transducer 30 provides the received reflection signal to electronics 32 where it is rectified and its envelop signal may be obtained. The envelop signal is transmit ted uphole over logging cable 34 to suitable surface electronics 36 where the amplitudes of the full wavelet of or the envelop of the full wavelet of the reflection signals are recorded in correlation with depth.

This process may be repeated above various producing zones throughout wellbore 18. The combined oil flow rates determined for producing zones below the zone being logged may be subtracted from the flow rate determined at the zone being logged to determine the oil flow rate from only that zone.

Figure 2:
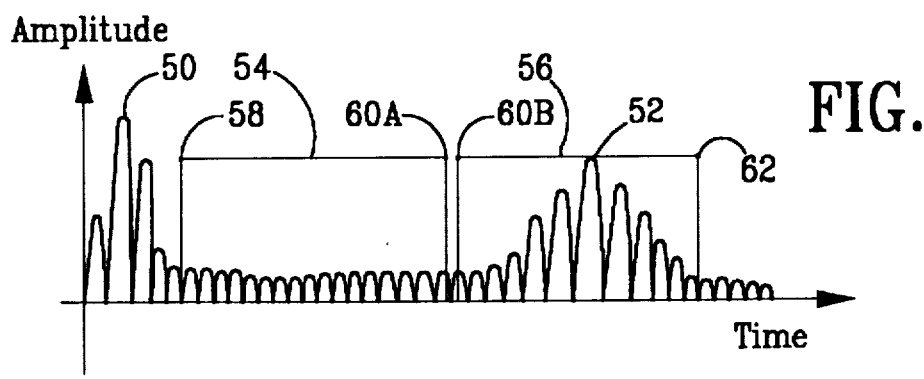
FIG. 2 is an illustration of a full wavelet signal that is typically received in an acoustic transceiver tool.
Figure 3:
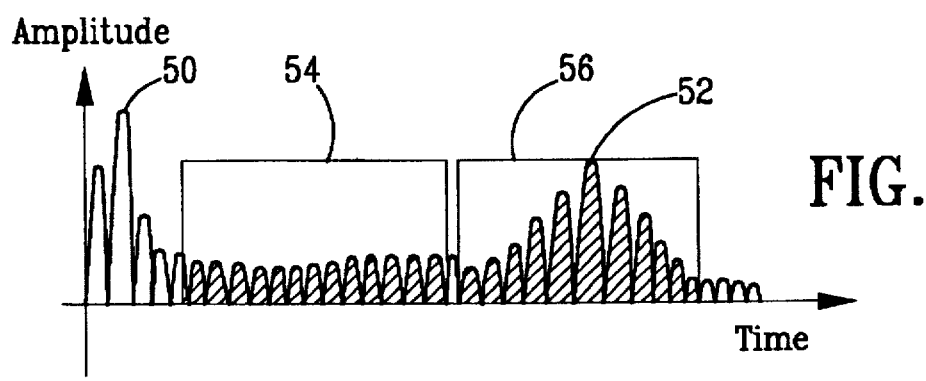
FIG. 3 is a graphical drawing illustrating the waveform received from acoustic energy compressional wave reflections from acoustic impedance changes in the fluid flow in the borehole of FIG. 1 with low gas holdup.
Figure 4:
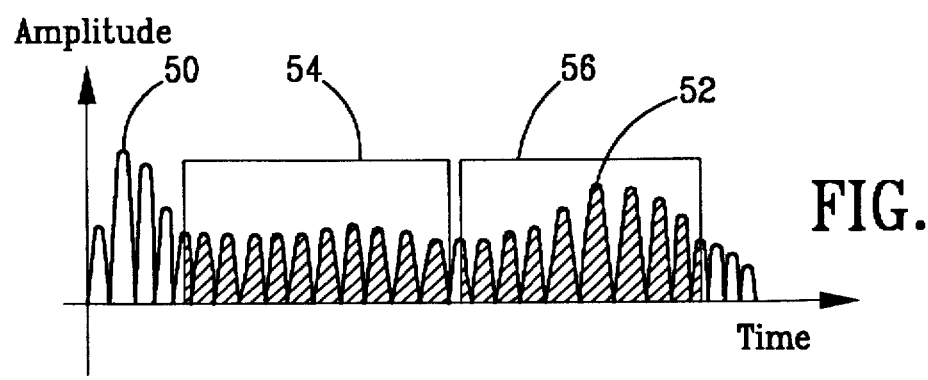
FIG. 4 is a graphical drawing illustrating the waveform received from acoustic energy compressional wave reflections from acoustic impedance changes in the fluid flow in the borehole of FIG. 1 with medium gas holdup.
Figure 5:
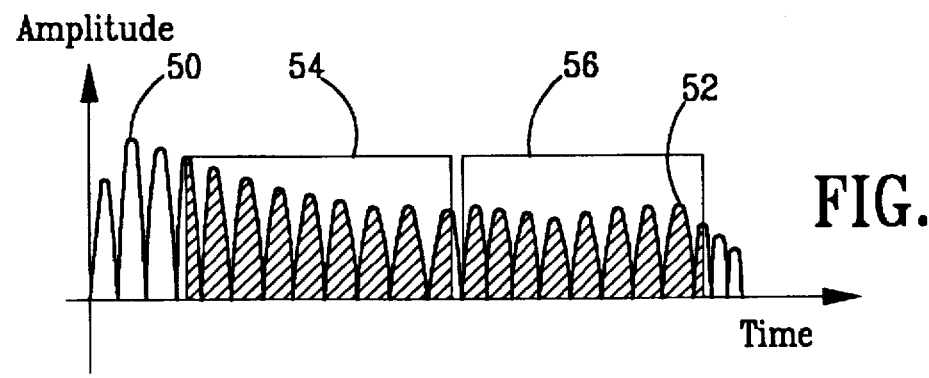
FIG. 5 is a graphical drawing illustrating the waveform received from acoustic energy compressional wave reflections from acoustic impedance changes in the fluid flow in the borehole of FIG. 1 with high gas holdup.
Figure 6:
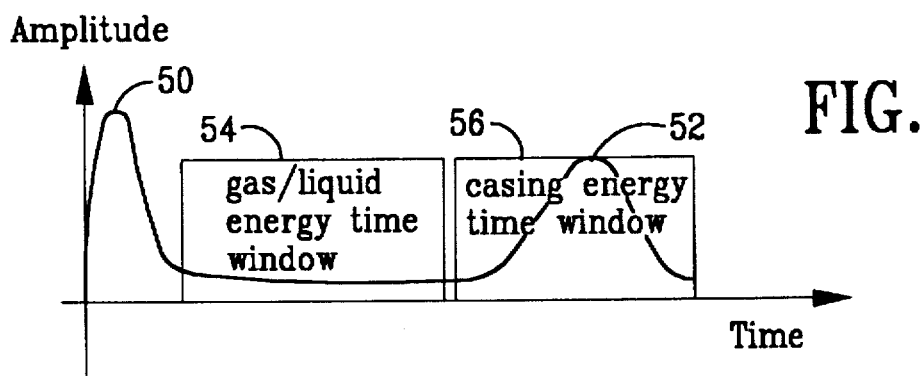
FIG. 6 is an illustration of an envelop signal obtained from the full wavelet signal of FIG. 2.
Figure 7:
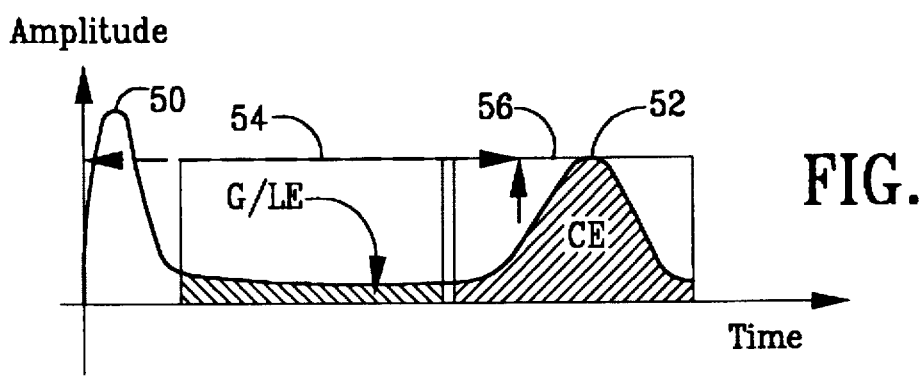
FIG. 7 is an illustration of an envelop signal obtained from the full wavelet signal of FIG. 3.
Figure 8:
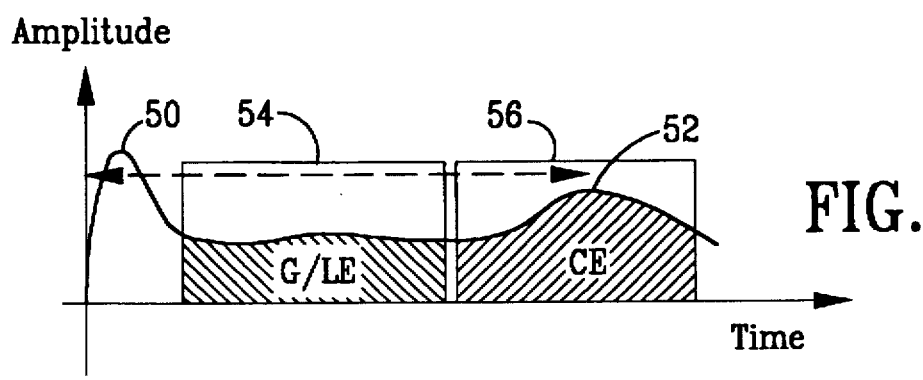
FIG. 8 is an illustration of an envelop signal obtained from the full wavelet signal of FIG. 4.
Figure 9:
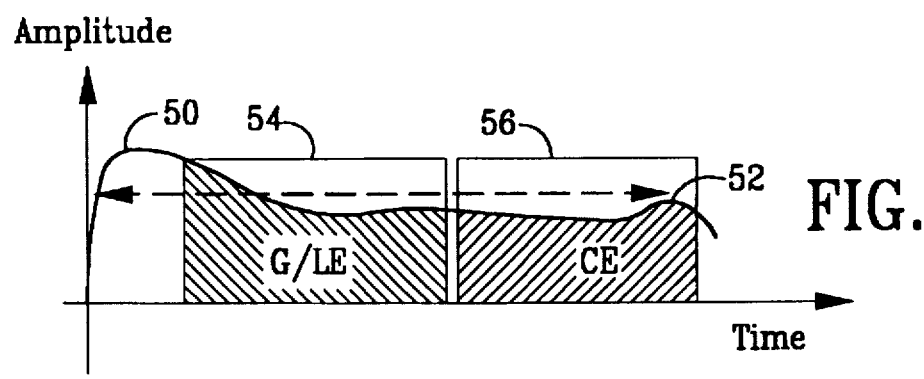
FIG. 9 is an illustration of an envelop signal obtained from the full wavelet signal of FIG. 5.

Regarding the envelop signal and the full wavelet signal, both signals are generated in the same manner. Using the borehole televiewer tool as the acoustical transducer, an acoustical transducer generates 300 kilohertz pressure waves. The pressure wave travels to the borehole wall, is reflected, comes back and is still a 300 kilohertz wave when detected. This type of signal is illustrated in FIG. 2. The full wavelet signal is affected by gas content in the fluid flow as illustrated in FIGS. 3-5. This type of signal is preferred in surface applications since this signal contains more accurate information concerning the quantities that it is used to delineate. Unfortunately this relatively high frequency signal cannot be transferred to the surface in a producing well very easily. What may be done in wellbore applications, as previously described, is to extract the envelop of this signal which is a much lower frequency and transfer it to the surface. At the surface a signal such as that shown in FIG. 6 is received. The effects of gas content in the fluid flow on the reflection signals is illustrated in FIGS. 7-9, which approximately correspond to the rectified full wavelet illustrations of FIGS. 3-5, respectively.

FIGS. 2-9 illustrate the full wavelet of the signal and the envelop of the full wavelet of the rectified signal as generally having two amplitude peaks 50 and 52 representing a primary reflection and an echo or casing reflection.

In each of the illustrations in FIGS. 2-5 and FIGS. 6-9, two time windows are set. These two areas are defined as a gas/liquid energy time window 54 and a casing energy window 56. Time window 54 begins at point 58 after peak 50 and ends at point 60A, prior to peak 52. Approximately at this point, point 60B, window 56 starts and ends after peak 56 at point 62. These two time windows are approximately the same width. The area under the curves in each of these windows is integrated to establish an area value for the gas/liquid energy time window and the casing energy time window. Once these two area values are determined, a ratio of the gas/liquid energy over the casing energy can be calculated to determine an indication of gas volume, R, defined as follows.

$$R = \frac{\text{gas/liquid energy}}{\text{casing energy}} = \frac{G/LE}{CE}$$

The more gas present in the fluid stream, the weaker the casing reflection is going to be. Also, the bubbles of gas in the fluid stream are going to reflect some energy. This energy is going to arrive at the transducer early in time. When the waveform is integrated, gas/liquid energy and casing energy are obtained. These values are used to establish a ratio as an indication of gas content. A large ratio value indicates a high content of hydrocarbon gas. Referring now to FIGS. 3, 4 and 5 and to FIGS. 7, 8 and 9 experimental data is illustrated that demonstrates this concept of no gas flow, medium gas flow, heavy gas flow. As illustrated, the amplitude peak of the casing reflection, peak 52, is reduced From FIG. 3 to FIG. 5 and in the envelop illustrations, from FIG. 7 to FIG. 9. This reduction in amplitude of the echo reflection is due to bubble energy, the energy dissipated in encountering gas bubbles in the fluid flow.

FIGS. 3 and 7 illustrate a situation with no or almost no gas holdup. FIG. 3 for the rectified full wavelet waveform and FIG. 7 for the envelop of the rectified full wavelet waveform. The ratio of gas/liquid energy to casing energy is approximately 0.3.

FIG. 4 illustrates the approximate rectified full wavelet waveform for a situation where medium gas holdup occurs. It is to be noted that in this situation the echo or casing reflection is diminished while reflections from the interfaces of density change for gas bubbles increases in time window 54. Thus the integral of the area under the curves in time window 54 increases while the integral of the area under the curves in time window 56 decreases. Thus, the ratio R, the indication of gas content, increases to a value of approximately 0.58, indicating a greater gas content in the fluid flow.

Similarly, FIG. 8 illustrates the envelop of the approximate rectified full wavelet waveform of FIG. 4 for a situation where medium gas holdup occurs. It is to be noted that in this situation the envelop of the echo or casing reflection is also diminished while the envelop of reflections from the interfaces of density change for gas bubbles increases in time window 54. Thus the integral of the area under the curves in time window 54 increases while the integral of the area under the curves in time window 56 decreases. Thus, the ratio R, the indication of gas content, increases to a value of approximately 0.6, indicating a greater gas content in the fluid flow. This ratio is slightly higher than the rectified full wavelet illustration due to smoothing at a higher amplitude level for the envelop in window 56 as opposed to window 54.

FIG. 5 illustrates the approximate rectified full wavelet waveform for a situation where high gas holdup occurs. In this situation the echo or casing reflection in time window 56 is diminished to the point of only slightly greater than the reflections from the interfaces of density change for gas bubbles in time window 54. Thus the integral of the area under the curves in time window 54 increases while the integral of the area under the curves in time window 56 decreases. Thus, the ratio R, the indication of gas content, increases to a value of approximately 1.2, indicating a greater gas content in the fluid flow.

Referring now to FIG. 9, the envelop of the approximate rectified full wavelet waveform of FIG. 5 is illustrated for a situation where high gas holdup occurs. In this situation the envelop of the casing reflection in time window 56 is diminished to the point of only slightly greater than the envelop of the reflections from the interfaces of density change for gas bubbles in time window 54. In fact, portions of the envelop curve in time window 56, the casing energy determining window, are lower than the majority of the envelop curve in time window 54, the gas/liquid energy determining window. Thus, the ratio R, the indication of gas content, increases to a value of approximately 1.2, indicating a greater gas content in the fluid flow. This ratio is approximately the same as the ratio in the rectified full wavelet illustration due to smoothing at the same amplitude level for the envelop in window 56 and window 54.

As illustrated, in the method of the present invention for determining the hydrocarbon flow rate in a horizontal fluid flow stream, an acoustic logging tool is placed in the stream. A beam of acoustic energy is directed from the logging tool toward the fluid flow. The beam of acoustic energy is detected when it reflects back to the acoustic logging tool. The reflected beam of acoustic energy is transformed into electrical signals. The electrical signals are rectified and transmitted to a location for processing. The flow rate of liquid hydrocarbons is determined from the full wavelet of the electrical signals.

In an alternate embodiment, the electrical signals are rectified and the envelop of the rectified electrical signals is determined. The envelop of the rectified electrical signals is transmitted to the location for further processing. The flow rate of liquid hydrocarbons is determined from the envelop of the electrical signals.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

We claim:

1. An apparatus for measuring fluid flow in a flow line comprising:

means for directing a beam of acoustic energy toward said fluid flow;

means for receiving reflection signals of said beam of acoustic energy;

means for rectifying said reflection signals;

means for defining two areas of said rectified reflection signals;

means for integrating said rectified reflected signals under each of said two areas to provide area integration values and to determine the portion of said fluid flow that is liquid; and means for determining a ratio of said integration values of said two areas of said envelop of said rectified reflection signals to determine gas content in said fluid flow.

2. The apparatus according to claim 1 wherein said means for defining includes:

means for identifying amplitude peaks representing a primary reflection and an echo reflection;

means for locating one area after said primary reflection amplitude peak; and means for locating a second area around said echo reflection amplitude peak.

3. The apparatus according to claim 2 wherein said means for locating said second area includes means for determining a casing reflection.

4. The apparatus according to claim 1 also including:

means for recording said rectified reflection signals.

5. The apparatus according to claim 4 also including:

means for determining total fluid flow from said recorded rectified reflection signals.

6. An apparatus for determining gas content in a multi-phase fluid flow in a flow line comprising:

means for directing a beam of acoustic energy toward said multi-phase fluid flow;

means for receiving reflection signals of said beam of acoustic energy;

means for rectifying said reflection signals;

means for determining an envelop of said rectified reflection signals of said beam of acoustic energy as a measure of fluid flow rate within the flow line;

means for defining two areas of said envelop of said rectified reflection signals;

means for integrating said envelop of said reflected signals in each area to provide area integration values; and means for determining a ratio of said integration values of said two areas of said envelop of said rectified reflection signals as an indication of gas content in said fluid flow.

7. The apparatus according to claim 6 wherein said means for defining includes:

means for identifying amplitude peaks representing a primary reflection and an echo reflection;

means for locating one area after said primary reflection amplitude peak; and means for locating a second area around said echo reflection amplitude peak.

8. The apparatus according to claim 7 wherein said means for locating said second area includes means for determining a casing reflection.

9. The apparatus according to claim 6 also including:

means for recording said rectified reflection signals.

10. The apparatus according to claim 9 also including:

means for determining total fluid flow from said recorded rectified reflection signals.

11. The apparatus according to claim 6 also including:

means for recording said envelop of said rectified reflection signals.

12. The apparatus according to claim 11 also including:

means for determining total fluid flow from said recorded envelop of said rectified reflection signals.

13. A method for measuring fluid flow in a flow line comprising the steps of:

directing a beam of acoustic energy toward said fluid flow;

receiving reflection signals of said beam of acoustic energy;

rectifying said reflection signals;

defining two areas of said rectified reflection signals;

integrating said rectified reflected signals within each area to provide area integration values; and determining a ratio of said integration values of said two areas of said envelop of said rectified reflection signals to provide an indication of gas content in said fluid flow.

14. The method according to claim 13 wherein said step of defining includes the steps of:

identifying amplitude peaks representing a primary reflection and an echo reflection;

locating one area after said primary reflection amplitude peak; and locating a second area around said echo reflection amplitude peak.

15. The method according to claim 14 wherein said step of locating said second area includes the step of determining a casing reflection.

16. The method according to claim 13 also including the step of:

recording said rectified reflection signals.

17. The method according to claim 16 also including the step of:

determining total fluid flow from said recorded rectified reflection signals.

18. A method for measuring fluid flow in a flow line comprising the steps of:

directing a beam of acoustic energy toward the fluid flow;

receiving reflection signals of said beam of acoustic energy;

rectifying said reflection signals;

determining an envelop of said rectified reflection signals of said beam of acoustic energy as a measure of fluid flow rate within the flow line;

defining two areas of said envelop of said rectified reflection signals;

integrating said envelop of said reflected signals in each area to provide area integration values; and determining a ratio of said integration values of said two areas of said envelop of said rectified reflection signals.

19. The method according to claim 18 wherein said step of defining includes the steps of:

identifying amplitude peaks representing a primary reflection and an echo reflection;

locating one area after said primary reflection amplitude peak; and locating a second area around said echo reflection amplitude peak.

20. The method according to claim 19 wherein said step of locating said second area includes the step of determining a casing reflection.

21. The method according to claim 18 also including the step of:

recording said rectified reflection signals.

22. The method according to claim 21 also including the step of:

determining total fluid flow from said recorded rectified reflection signals.

23. The method according to claim 18 also including the step of:

recording said envelop of said rectified reflection signals.

24. The method according to claim 23 also including the step of:

determining total fluid flow from said recorded envelop of said rectified reflection signals.

* * * * *